US012453540B2

(12) United States Patent
Iqbal et al.

(10) Patent No.: US 12,453,540 B2
(45) Date of Patent: Oct. 28, 2025

(54) DIGITAL ENDOSCOPE

(71) Applicant: Surgease Innovations Limited, Nelson Lancashire (GB)

(72) Inventors: Fareed Iqbal, Nelson (GB); Gillian Gole-Cruz, Windsor Berkshire (GB); Robin Crossley, Windsor Berkshire (GB); Jeremy Gardner, Windsor Berkshire (GB)

(73) Assignee: Surgease Innovations Limited, Nelson (GB)

( * ) Notice: Subject to any disclaimer, the term of this patent is extended or adjusted under 35 U.S.C. 154(b) by 831 days.

(21) Appl. No.: 17/284,053

(22) PCT Filed: Oct. 10, 2019

(86) PCT No.: PCT/GB2019/052891
§ 371 (c)(1),
(2) Date: Apr. 9, 2021

(87) PCT Pub. No.: WO2020/074913
PCT Pub. Date: Apr. 16, 2020

(65) Prior Publication Data

US 2021/0386411 A1 Dec. 16, 2021

(30) Foreign Application Priority Data

Oct. 10, 2018 (GB) ..................................... 1816514

(51) Int. Cl.
*A61B 10/04* (2006.01)
*A61B 1/00* (2006.01)
(Continued)

(52) U.S. Cl.
CPC .......... *A61B 10/04* (2013.01); *A61B 1/00068* (2013.01); *A61B 1/00087* (2013.01);
(Continued)

(58) Field of Classification Search
CPC ............ A61B 1/00064; A61B 1/00066; A61B 1/00068; A61B 1/00087; A61B 1/00096;
(Continued)

(56) References Cited

U.S. PATENT DOCUMENTS 3,548,822 A * 12/1970 Seeler ............... A61M 16/0084 128/203.11
3,561,429 A * 2/1971 Jewett .................... A61B 10/04 606/171
(Continued)

FOREIGN PATENT DOCUMENTS

CN 1794944 A 6/2006
CN 103841880 A 6/2014
(Continued)

OTHER PUBLICATIONS

DE-202017103690-U1 English Translation (Year: 2017).*
(Continued)

*Primary Examiner* — Charles A Marmor, II
*Assistant Examiner* — Andrew E Hoffpauir
(74) *Attorney, Agent, or Firm* — Greenberg Traurig LLP; Roman Fayerberg; Jaime Burke

(57) ABSTRACT

A portable digital rectosigmoidoscope single-handed, digital intestinal endoscope, used by suitably trained healthcare workers to digitally view the anus, rectum and distal sigmoid colon in people with anorectal symptoms at point of care.

27 Claims, 6 Drawing Sheets

(51) Int. Cl.

| | |
|---|---|
| ***A61B 1/015*** | (2006.01) |
| ***A61B 1/018*** | (2006.01) |
| ***A61B 1/31*** | (2006.01) |
| ***A61M 13/00*** | (2006.01) |

(52) U.S. Cl.
CPC ...... *A61B 1/00096* (2013.01); *A61B 1/00103* (2013.01); *A61B 1/00105* (2013.01); *A61B 1/015* (2013.01); *A61B 1/018* (2013.01); *A61B 1/31* (2013.01); *A61M 13/003* (2013.01); *A61M 2210/1064* (2013.01); *A61M 2210/1067* (2013.01)

(58) Field of Classification Search
CPC ............ A61B 1/00103; A61B 1/00105; A61B 1/00108; A61B 1/015; A61B 1/018; A61B 1/31; A61B 10/04; A61M 2210/1064; A61M 2210/1067; A61M 13/003; A61M 16/0063; A61M 16/0075; A61M 16/208
See application file for complete search history.

(56) References Cited

U.S. PATENT DOCUMENTS

| | | | | |
|---|---|---|---|---|
| 4,258,721 | A | 3/1981 | Parent et al. | |
| 4,598,698 | A * | 7/1986 | Siegmund ................ | A61B 1/12 600/156 |
| 5,083,549 | A * | 1/1992 | Cho ..................... | A61B 18/245 600/129 |
| 5,860,953 | A * | 1/1999 | Snoke .................. | A61B 1/0052 604/95.04 |
| 6,328,734 | B1 * | 12/2001 | Zappala ................. | A61B 18/14 606/46 |
| 6,447,444 | B1 | 9/2002 | Avni et al. | |
| 6,540,670 | B1 * | 4/2003 | Hirata .................. | A61B 1/0051 600/152 |
| 6,605,036 | B1 | 8/2003 | Wild | |
| 7,306,574 | B2 | 12/2007 | Massey et al. | |
| 8,235,889 | B2 | 8/2012 | Kohno | |
| 8,460,182 | B2 | 6/2013 | Ouyang et al. | |
| 2003/0135230 | A1 | 7/2003 | Massey et al. | |
| 2005/0059992 | A1 * | 3/2005 | Leiboff ................. | A61M 31/00 606/197 |
| 2005/0075538 | A1 * | 4/2005 | Banik .................. | A61B 1/0052 600/152 |
| 2005/0234391 | A1 * | 10/2005 | Uesugi ................... | A61B 50/10 604/24 |
| 2005/0245789 | A1 * | 11/2005 | Smith .................. | A61B 1/0016 137/560 |
| 2006/0241348 | A1 | 10/2006 | Kohno | |
| 2006/0258955 | A1 | 11/2006 | Hoffman et al. | |
| 2008/0058595 | A1 * | 3/2008 | Snoke .................... | A61B 17/42 600/114 |
| 2009/0209813 | A1 * | 8/2009 | Lubowski ................ | A61B 1/31 600/156 |
| 2010/0010308 | A1 * | 1/2010 | Braun ................ | A61B 1/00142 600/121 |
| 2010/0168520 | A1 * | 7/2010 | Poll ........................ | A61B 1/126 600/169 |
| 2010/0324483 | A1 * | 12/2010 | Rozenberg .......... | A61M 16/045 607/113 |
| 2012/0029429 | A1 * | 2/2012 | Klein .................... | A61M 5/172 604/151 |
| 2012/0289858 | A1 | 11/2012 | Ouyang et al. | |
| 2014/0187859 | A1 * | 7/2014 | Leeuw ................ | A61M 13/003 600/114 |
| 2014/0200402 | A1 * | 7/2014 | Snoke ................ | A61B 1/00121 600/104 |
| 2014/0213850 | A1 * | 7/2014 | Levy ...................... | A61B 1/018 600/156 |
| 2015/0133779 | A1 * | 5/2015 | Yurek .................... | A61B 8/481 600/435 |
| 2016/0120395 | A1 * | 5/2016 | Qi ............................ | A61B 1/04 600/123 |
| 2016/0192822 | A1 * | 7/2016 | Ofir ...................... | A61B 1/0011 600/129 |
| 2018/0184892 | A1 | 7/2018 | Truckai et al. | |
| 2020/0205644 | A1 * | 7/2020 | Nakajima ............ | A61B 1/3132 |
| 2020/0214543 | A1 * | 7/2020 | Ben-Arye .......... | A61B 1/00103 |
| 2021/0030261 | A1 * | 2/2021 | Kress ................. | A61B 1/00094 |

FOREIGN PATENT DOCUMENTS

| | | | | |
|---|---|---|---|---|
| DE | 202017103690 | U1 * | 8/2017 | ............. A61B 17/00 |
| EP | 1707107 | A1 | 10/2006 | |
| WO | 2016182463 | A1 | 11/2016 | |
| WO | 2018016605 | A1 | 1/2018 | |

OTHER PUBLICATIONS

Anderson et al., "Surgical vs general practitioner assessment: diagnostic accuracy in 2-week-wait colorectal cancer referrals," Colorectal Disease: The Official Journal of the Association of Coloproctology of Great Britain and Ireland, 2011, vol. 13, No. 8, pp. e212-e215.
Atkin et al., "Once-only flexible sigmoidoscopy screening in prevention of colorectal cancer: a multicentre randomised controlled trial," The Lancet, May 8, 2010, vol. 375, No. 9726, pp. 1624-1633.
Rao et al., "Comparison of rigid vs flexible sigmoidoscopy in detection of significant anorectal lesions," Colorectal Disease: The Official Journal of the Association of Coloproctology of Great Britain and Ireland, 2005, vol. 7, No. 1, pp. 61-64.
International Search Report for corresponding International Patent Application No. PCT/GB2019/052891, mailed Jan. 17, 2020 (5 pages).

* cited by examiner

SECTION K-K

Bottom Cross Section

DIGITAL ENDOSCOPE

CROSS REFERENCE TO RELATED APPLICATIONS

This application is a U.S. National Phase patent application of PCT International Application No. PCT/GB2019/052891, filed Oct. 10, 2019, which claims priority to and the benefit of GB Application No. 1816514.2, filed on Oct. 10, 2018, the entire contents of each of which are hereby incorporated by reference in their entireties.

The present invention relates to a digitally enhanced optical rigid sigmoidoscope that provides illumination and digital visualisation of the anus, rectum and sigmoid colon at point of care delivery.

The invention enables digital images of the lower colon, rectum and anus to be captured, stored and shared for diagnostic, training and evidential purposes and for surveillance to track disease progression and treatment outcomes. Preferably via a bespoke integrated imaging software platform.

BACKGROUND

Colorectal cancer (CRC) is the third most commonly diagnosed malignancy and the fourth leading cause of cancer-related deaths in the World. There is wide geographical variation in incidence with rates varying ten-fold in both sexes worldwide.

The number of new cases is expected to increase by 60% to more than 2.2 million cases and 1.1 million cancer deaths by 2030.

Survival rates are directly proportional to early diagnosis.

Detection of disease at stage I carries a survival rate of up to 94%.

Detection of disease at stage II carries a survival rate of up to 82%.

Detection of disease at stage III carries a survival rate of up to 67%.

Detection at stage IV carries a survival rate of up to 11%.

Approximately half of bowel cancers are diagnosed at a late stage; stage 3 and 4 where treatments are less effective and premature death is more likely.

Screening is a general term used to describe the evaluation of a patient for the presence of pre-cancers or early cancers before the onset of symptoms. Screening aims to find disease at an early stage where survival and outcomes are more favourable. Bowel cancer screening is conducted routinely in patients meeting one or more eligibility criteria. Alternatively, screening may be conducted following a patient or clinician request. A request for bowel screening may be made in the presence or absence of symptoms.

Alternatively, bowel screening may be conducted as part of a population wide screening program.

Screening programs operate in some countries notably the USA and the UK. However New Zealand has no screening program even though rectal cancer death is the leading cause of cancer related death amongst the Maori.

In countries where screening is available, it generally commences at or around the age of 55 and is repeated periodically (typically every two years) until the age of 74. Screening can detect bowel cancer or pre-cancers at an early stage, when treatments are more effective. Bowel screening can also be used to identify and remove precancerous growths or polyps in the bowel and thus prevent the onset of cancer. There is an established and widely accepted evidence-base that screening saves lives and prevents premature deaths.

Bowel cancer rates are increasing in younger populations with rates doubling annually in people aged under 45.

Up to 42% of malignancies occur within the first 25 cm from the anal verge. These are referred to as rectal cancers. Rectal cancers have a poorer prognosis than tumours of the same grade and stage which occur beyond 25 cm from the anal verge.

A range of invasive and non-invasive bowel cancer screening tests are currently available by way of example only.

Faecal Immunochemical Test (FIT)

FIT testing is a simple, reliable and cheap laboratory based analysis of a home-based test.

The patient collects a single stool sample at home and sends it to a laboratory for analysis. There is minimal embarrassment and compliance rates are reasonable with rates varying from 60% to 70%.

The FIT test identifies the presence of blood in the stools which can be a marker of a cancer. If a positive result is obtained further investigation is indicated which conventionally includes a colonoscopy or colon-based CT scans.

Older faecal testing kits use a guaiac-based technology (gFOBT) which tests for blood in three separate faecal samples. The guaiac test is gradually being replaced in the UK by FIT which is more acceptable to patients as its relies on a single test. The adoption of FIT is expected to increase compliance with screening and lead to a surge in demand for endoscopy by at least 100,000 procedures per year in the UK alone.

Flexible Sigmoidoscopy/Bowel Scope Screening is an invasive screening test which enables the lower colon to be examined and biopsied if necessary.

The flexible sigmoidoscope is inserted via the anus to allow inspection. The colon is insufflated with an external air source to insufflate the colon and to open up mucosal folds for better visualisation. A flexible sigmoidoscope can be used to inspect, and biopsy the rectum, the sigmoid and the descending colon. Between 49% and 62% of all colorectal malignancies can be reached by a flexible sigmoidoscope.

The Bowel scope programme in the UK currently offers all patients a single endoscopic examination with a flexible sigmoidoscope when they reach 55 years of age. This screening intervention can reduce a person's probability of dying from colorectal cancer by 40% over their life-time. Atkin W S, Edwards R, Kralj-Hans I, Wooldrage K, Hart A R, Northover J M, et al. Once-only flexible sigmoidoscopy screening in prevention of colorectal cancer: a multicentre randomised controlled trial. Lancet. 2010; 375(9726):1624-33.

During flexible sigmoidoscopy, polyps or pre-cancerous growths can be identified and removed, and/or one or more biopsy can be performed if abnormal areas of the colon are seen.

Flexible sigmoidoscopy is an invasive procedure which is only available in formal endoscopy units where strict adherence to governance and quality performance frameworks must be satisfied annually. The endoscopic equipment must undergo high level disinfection and sterilisation between each patient which is time consuming and expensive.

Regulatory bodies in the UK, such as NICE, have recommended the use of endoscopy when the risk of malignancy is 3% or more. As a result, endoscopy services remain the single most strained diagnostic service in the NHS and in healthcare systems in most developed nations.

Visits to endoscopy departments require a separate hospital appointment prior to which the patient must be been counselled, and consented.

The patient must undergo mechanical bowel preparation up to 24 hours in advance of the examination.

These limitations prevent clinicians from making immediate diagnoses when patients first present in outpatient clinics. As a result of these limitations risk averse clinicians cannot safely rule out disease particularly in the very young or otherwise low risk patients and are therefore inclined to over refer for colonoscopy which is an expensive and unpleasant procedure.

The large referral burden, is placing great strains on colonoscopy suites which are scarce, expensive to establish, operate and staff.

Rigid Sigmoidoscopy/Proctoscopy

Conventional bedside examination of the anus and rectum is limited to proctoscopy and rigid sigmoidoscopy. These practices rely on the use of inert disposable plastic tubes known as proctoscopes and rigid sigmoidoscopes which have inbuilt or external light-sources.

In current clinical practice, rigid sigmoidoscopy is typically used to make a luminal assessment of the distal gastrointestinal tract; up to 25 centimetres from the anal verge. The typical instrument arrangement consists of four main components: a light source (either internal or external), a rigid tube/sheath with an obturator, a head with sealed viewing window and fibre optic light connection) and an insufflation bellows. A typical system permits the introduction of biopsy forceps, tubes, needles and other instruments, though the views are obscured and it is performed in a non-air-tight condition as when the viewing window is opened, bowel insufflation is lost which can lead to missed cancers and errors in sampling. Increasingly, rigid sigmoidoscope sets are disposable single use systems, produced by companies such as Rocket Medical Ltd and THD-UK Ltd. Most are self-lubricating and scope lengths average between 20-25 centimetres with diameters of up to 24 centimetres. The rigid tube is first inserted into the anus by means of an obturator which acts as a smooth trocar to navigate the firm anal muscles. Once inserted the obturator is removed from the proximal end and the glass window is closed. The glass window is also the delivery mechanism for light which can be internally or externally sourced. A connected bellows is then squeezed to deliver air into the rectum by the other hand and a view is obtained by looking directly down the optical window.

Reusable rigid sigmoidoscopes made from stainless steel are also known and require high-level disinfection between uses.

Conventional rigid sigmoidoscopy and proctoscopy systems are impractical, costly due to reprocessing costs, difficult to use and have poor patient satisfaction and diagnostic value Rao V S, Ahmad N, Al-Mukhtar A, Stojkovic S, Moore P J, Ahmad S M. Comparison of rigid vs flexible sigmoidoscopy in detection of significant anorectal lesions. Colorectal disease: the official journal of the Association of Coloproctology of Great Britain and Ireland. 2005; 7(1):61-4.

Anderson O, Afolayan J O, Ni Z, Bates T. Surgical vs general practitioner assessment: diagnostic accuracy in 2-week-wait colorectal cancer referrals. Colorectal disease: the official journal of the Association of Coloproctology of Great Britain and Ireland. 2011; 13(8):e212-5.

Because of the inherent challenges in performing these procedure they have largely been abandoned by most specialists.

Even a skilled surgeon may find the process awkward, uncomfortable and difficult to perform. Rigid sigmoidoscopy has a fixed handle which requires the clinician to bend down excessively, use two hands to operate and hyper rotate their wrist to manoeuvre the sigmoidoscope into position.

Also, in larger patients accurate positioning of the sigmoidoscope may be impeded by the buttocks.

If the sigmoidoscope needs to be repositioned to secure a complete 360° view of the lower colon and rectum or there is a requirement to remove a biopsy specimen, there is often a tendency to rest and pivot the scope on the patient's anus which is painful for the patient.

Air is pumped into the rectum via the device using a bladder and hand pump arrangement (bellows) which is an awkward two-handed operation, made more difficult in larger patients where the buttocks must be supported to permit accurate positioning of the sigmoidoscope.

The operator must position themselves appropriately to permit viewing through the sigmoidoscope which may be difficult, obscured, partial or awkward for the operator depending on the specific anatomy of the patient. It also makes the procedure inheritably unhygienic as it requires the face of the operator to be in close proximity to the patients buttocks and anus.

Examinations performed using this technique are rudimentary and often unreliable as the clinician has only a small and awkward field of view.

Furthermore the reusable elements are hard to clean and present an infection risk whilst the disposable elements are expensive. The air filters, which must be changed between each patient, are difficult to remove and replace hence surgeons may be reluctant to change filters which presents an additional risk of cross-infection.

Conventional rigid sigmoidoscopy has only ever used as an adjunct to be used in combination with detailed examinations using colonoscopy.

Patients need to be admitted to hospital, which is costly, time consuming, embarrassing and further reduces patient compliance.

Patient and clinician satisfaction of the procedure may be compromised as there is no way of capturing, storing or sharing images with the patient or colleagues or for surveillance purposes.

Colonoscopy

Colonoscopy is an invasive, expensive, hospital based investigation which can only be performed in a surgical setting by a highly skilled specialist gastroenterologist as it carries a low risk of perforation which may require surgery.

Prior to the procedure, the patient must undergo bowel preparation by taking oral agents that mechanically empty the bowel. This is distressing and is unsuitable in patients with poor mobility and poor renal function. It can also lead to faecal incontinence. On the day of the procedure, the gastroenterologist inserts a viewing tube (colonoscope) into the rectum for the purpose of inspecting the colon. During colonoscopy, polyps or pre-cancerous growths can be removed, bleeding can be cauterized, and a biopsy can be performed if abnormal areas of the colon are seen.

Colonoscopy is a procedure that enables a gastroenterologist to evaluate the inside of the colon (large intestine or large bowel) along its full length. The colonoscope is a four-foot long, flexible tube about the thickness of a finger with a camera and a source of light at its tip. The tip of the colonoscope is inserted into the anus and advanced slowly, under visual control, into the rectum and through the colon usually as far as the cecum, which is the first part of the colon.

Colonoscopy may be performed for a variety of reasons. The vast majority of colonoscopies are performed as part of screening program for colon cancer or to exclude cancer when symptoms are present. These include blood in the stool, abdominal pain, diarrhoea, a change in bowel habit, or an abnormality found on colonic X-rays or a computerized axial tomography (CT) scan.

Colonoscopy is embarrassing, invasive, inconvenient and unpleasant for the patient and requires complete or partial sedation with the associated costs and risks.

Depending on the nature of any symptoms a patient may be offered one or more bowel screening tests.

FIT/FOBt screening can also be used to assess suitability for colonoscopy. Sigmoidoscope screening can also be used to assess suitability for colonoscopy.

Global demand for colonoscopy is increasing annually. Using the current screening protocols estimated referral rates for colonoscopy in the UK alone are predicted to reach 1.7 million by 2020. A need exists to reduce the number of colonoscopy referrals.

To reduce unnecessary colonoscopy referrals and improve the diagnostic accuracy of a range of life threatening and serious diseases there, is a pressing need for a comfortable, reliable, efficient, cost-effective and simple screening method to triage anorectal symptoms. The procedure should be performed safely and by lower skilled non-specialists. Offering these procedures in a primary health care setting can also improve patient compliance and provide rapid, reliable diagnosis without the need for hospital visits or further investigations.

There is a further need for a procedure which allows the identification, surveillance and treatment of rectal lesions, malignancy or other disease. A yet further need exists for a means of quickly and easily capturing high quality endoscopic visualisation data at the bedside by relatively low skilled health care professionals, thus avoiding a referral to a formal endoscopy suite.

U.S. Pat. No. 6,447,444 describes a video endoscope having a generally rigid; elongate insertion member having distal and proximal ends, and a video camera head fixed at the distal end of the insertion member. A sheath fits over and covers the insertion member, the sheath having a distal portion covering the video camera head, at least a section of which distal portion is substantially transparent. The distal portion of the sheath further including a narrowed tip comprising two or more leaves which are closed during insertion through the anus and open apart after insertion to expose the transparent section of the distal portion of the sheath.

SUMMARY OF THE INVENTION

According to the invention there is provided a rigid scope (125) comprising:

a rigid shaft (1) and a handle (100) for releasable attachment to the rigid shaft (1); and wherein the handle (100) comprises a detachable lumened manifold (5); and an integrated pressurised gas supply.

In some embodiments, the gas supply is provided by: a bellows (6), a hand pump, an electric pump, a gas cartridge, or a gas canister.

In some embodiments, the lumened manifold (5) comprises one or more channel (13,14,15) for receiving one or more of: a camera; a surgical instrument, a biopsy forceps, pressurised gas, a cauterising coil and a light source.

In some embodiments, one or more of the channels further comprise a one-way valve (17, 18. 19). In some embodiments, the valve is a dome valve. In some embodiments, one or more channels (13,14,15) comprise one or more microfilter.

In some embodiments, the rigid scope further comprises one or more of: a lens; and a port for accessing the one or more channel. In some embodiments, the rigid scope further comprises a gas releaser (7) for use in releasing gas from the patient.

In some embodiments, one or more of the shaft and the manifold are single use. In some embodiments, the shaft (1) is tapered the proximal end of the shaft having a diameter which exceeds the diameter of the distal end of the shaft.

In some embodiments, the shaft 1 and the handle 100 are arranged at an approximately 20 degree angle to one another. In some embodiments, the shaft further comprises a biopsy channel 4. In some embodiments, the shaft 1 further comprises a graticule.

In another aspect of the invention there is provided a lumened manifold for use with a rigid scope (125) as herein described.

In further aspect the invention relates to a one-handed method of viewing the anus, rectum or lower colon.

In further aspect the invention relates to a rigid scope for use in the sampling of the rectum and sigmoid colon.

In further aspect the invention relates to a method of treatment comprising inserting a scope into the lower colon and sampling, performing biopsy, removing, cauterizing or otherwise treating the lower colon.

In further aspect the invention relates to a method of anorectal diagnosis comprising inserting the rigid scope into the anus, rectum or lower colon, viewing, performing biopsy or otherwise examining the anus, rectum or lower colon, and comparing the results with images or biopsies of known normal anus, rectum or lower colon to diagnose disease.

In further aspect the invention relates to a method of diagnosis or treatment comprising the method herein described In one aspect, there is provided a method of diagnosis and treatment, optionally to the anorectal region, comprising a) inserting a rigid scope as claimed in any one of claims 1 to 13 into the anus, rectum or lower colon, viewing, performing biopsy or otherwise examining the anus, rectum or lower colon, and comparing the results with images or biopsies of known normal anus, rectum or lower colon to diagnose disease; and b) treating the anus, rectum or lower colon according to the disease diagnosis in a).

DESCRIPTION OF THE FIGURES

The invention will now be described with reference to the accompanying diagrammatic drawings in which.

DETAILED DESCRIPTION

The invention relates to a portable digital device. It may be described as a sigmoidoscope, for example a rectosigmoidoscope device. It may be used single-handedly. It may also be described as a digital intestinal endoscope. Optionally, it may be used by suitably trained healthcare workers to digitally view the anus, rectum and colon (optionally the distal sigmoid colon) in people with some or no anorectal symptoms at point of care. In some embodiments, the rigid scope is a digital endoscope.

The invention will now be described with reference to the figures.

Figure 1:
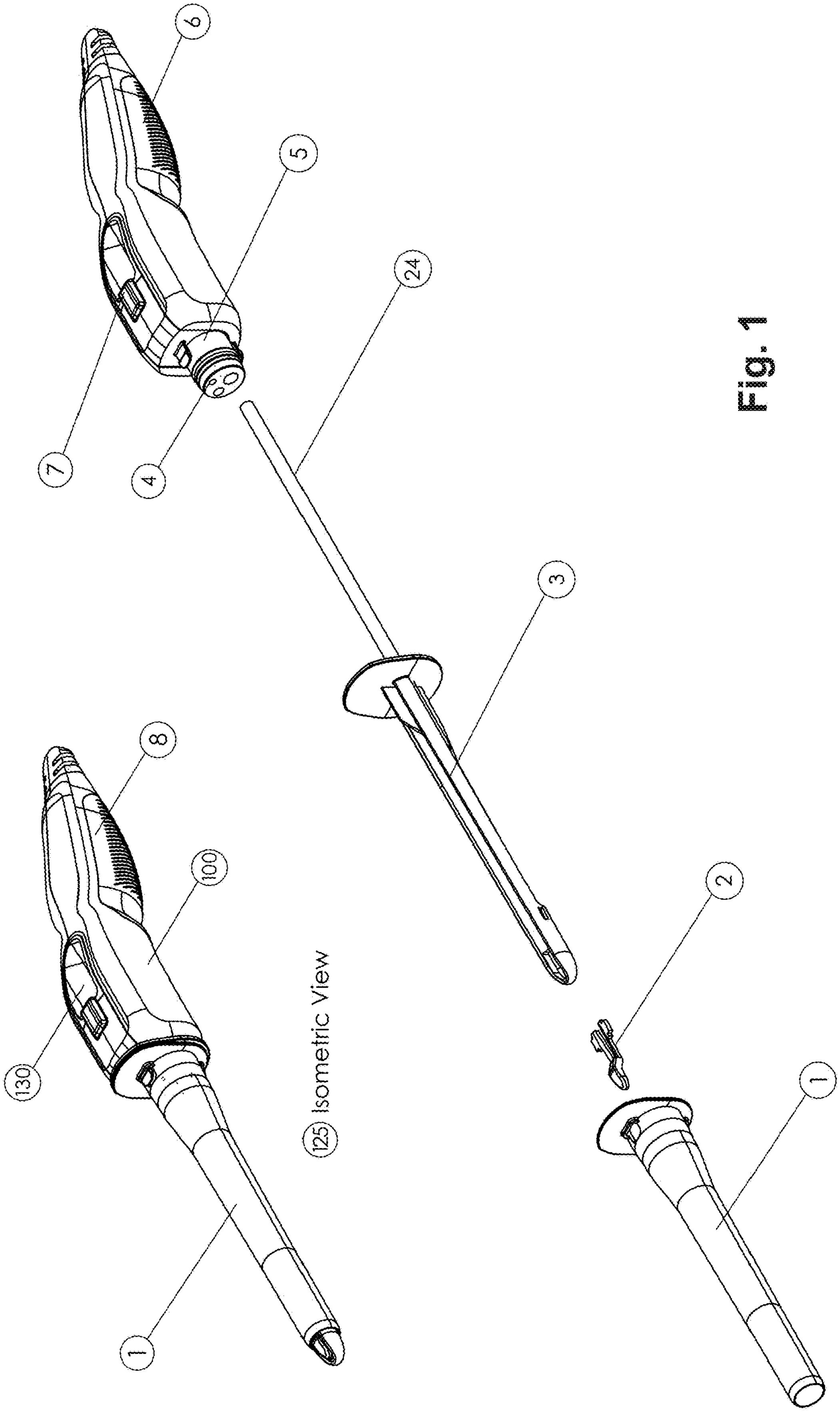
FIG. 1 is a schematic overview of the invention assembled and disassembled to show the separate components of the device.
Figure 2:
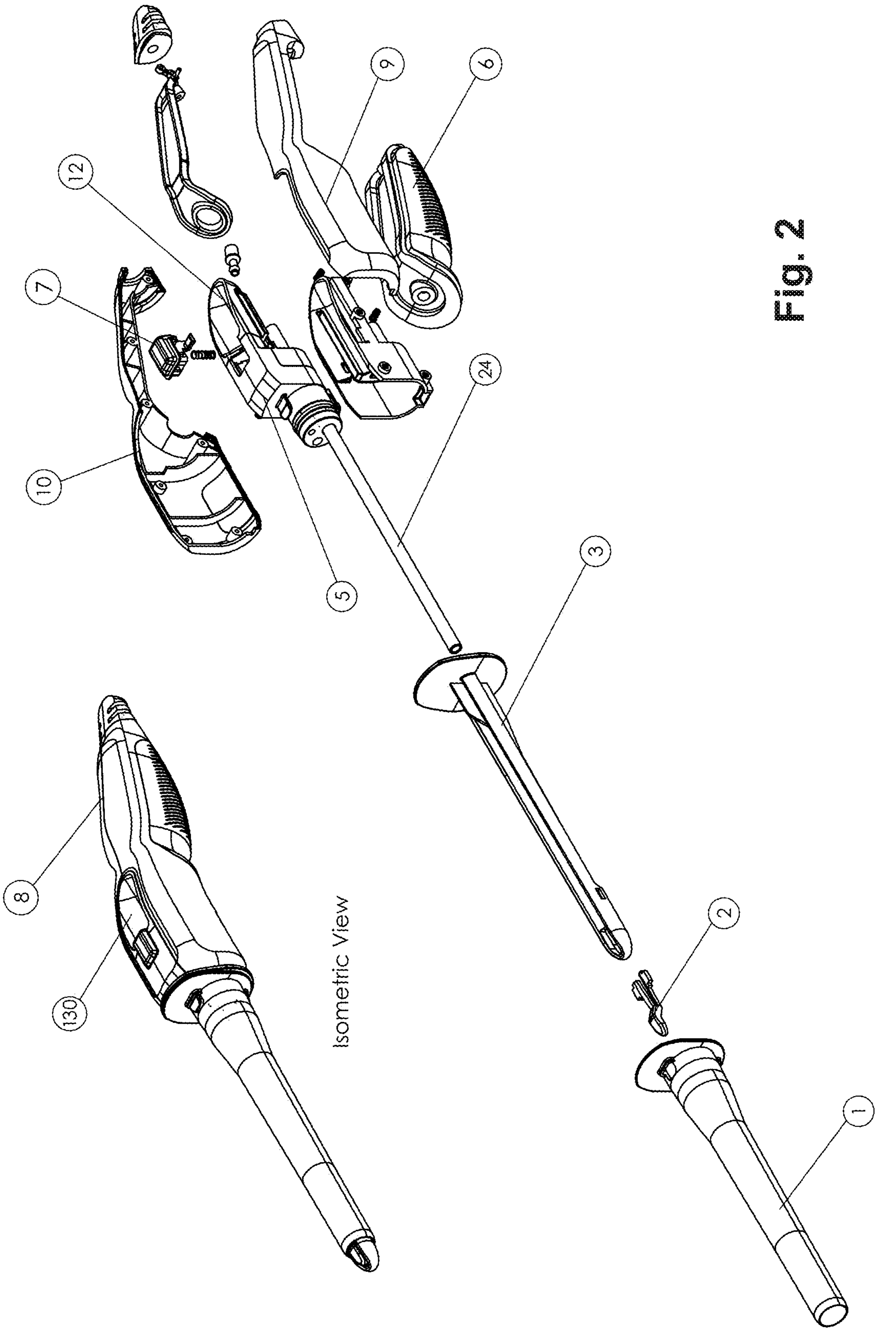
FIG. 2 is an exploded view of the key elements of the device.
Figure 3:
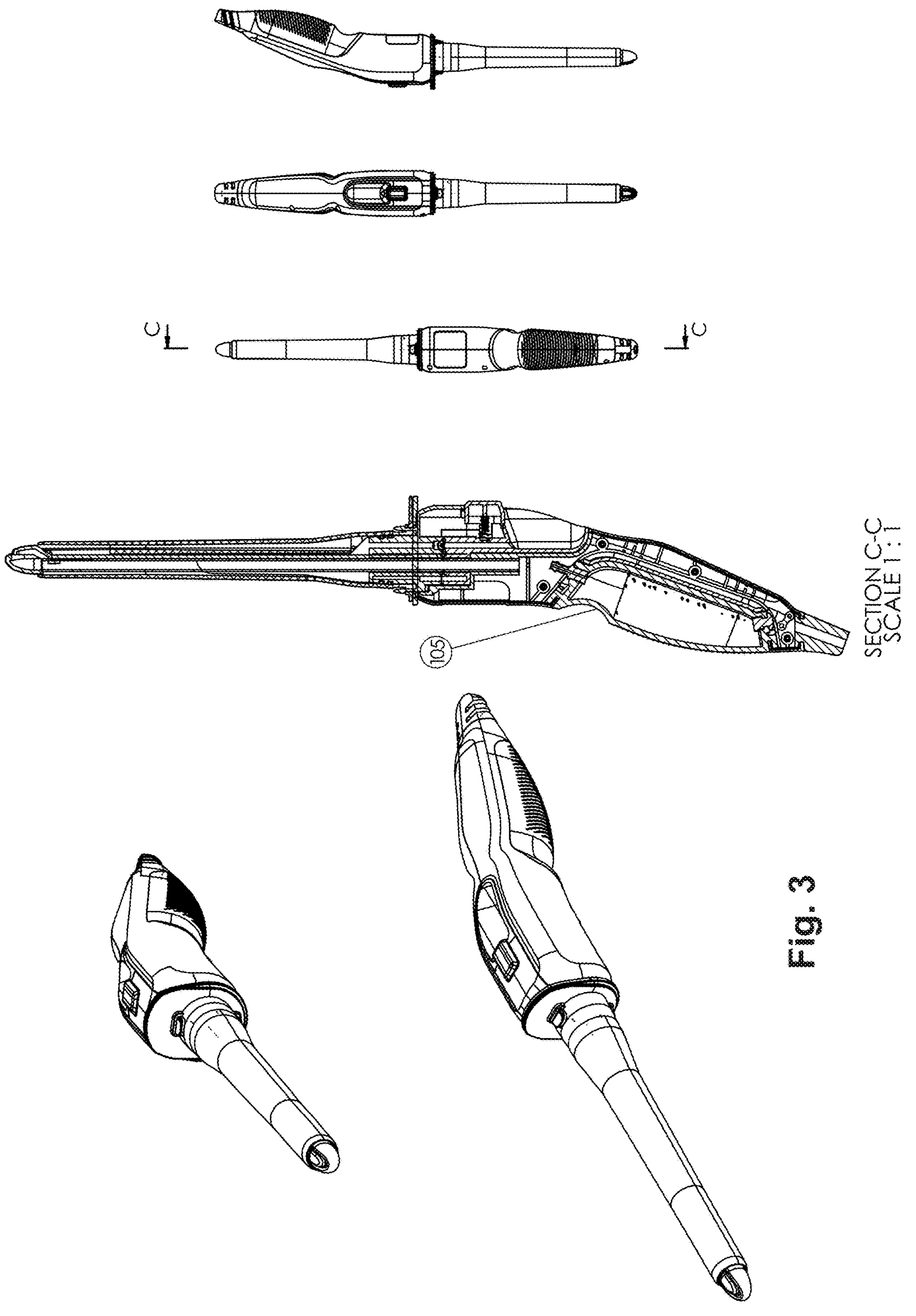
FIG. 3 is view showing the bellows arrangement in the handle in a preferred embodiment.

As shown in FIGS. 1, 2 and 3 the invention comprises a reusable rigid scope, proctoscope, rectoscope, sigmoidoscope, endoscope (these terms will be used interchangeably herein).

The sigmoidoscope 125 comprises a disposable rigid outer shaft 1 for insertion into the anus and a reusable handle 100.

Preferably the shaft 1 is sized and shaped to allow it to be comfortably inserted into a patient's lower colon, without risking damage to the structures.

The disposable rigid sigmoidoscope shaft 1 releasably engages with the reusable handle 100.

The handle 100, made up of two plastic enclosures 9,10, further comprises a disposable manifold 5 a camera channel 24 and a reusable handgrip 8 sized and shaped to be held and operated by a single hand of the operator.

The handle 100 remains outside the patient throughout the procedure.

Preferably the shaft 1 has a circular cross section and is tapered so that the distal end of the shaft is narrower than the proximal end of the shaft closest to the handle. A narrower distal end makes it more comfortable for the patient during insertion. A wider proximal end permits the introduction and manipulation of surgical instruments and provides capacity to accommodate a three or more lumened disposable manifold 5.

The shaft 1 for use in adults is preferably approximately 18 cm in length to allow the 25 cm of the lower colon closest to the anal verge to be examined, sampled or treated.

Figure 6:
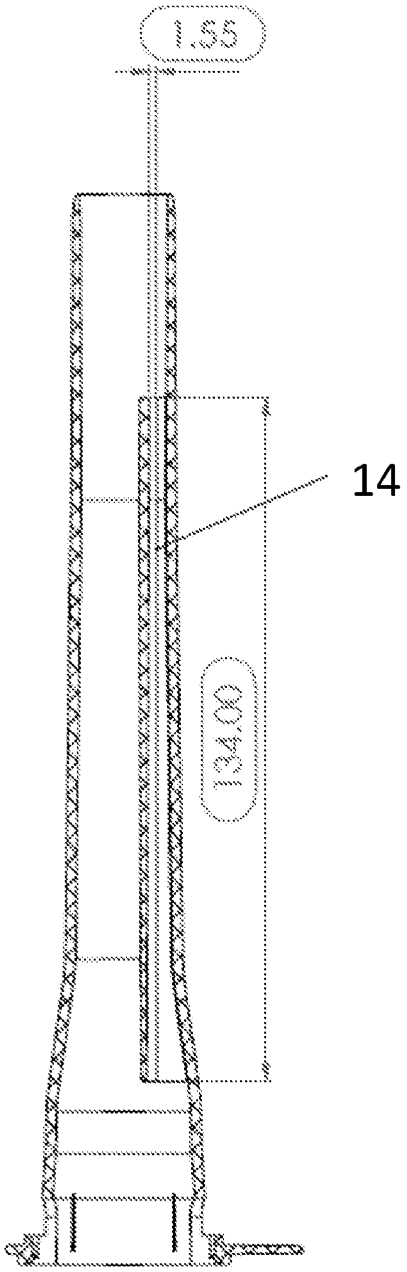
FIG. 6 shows the shaft from a variety of different angles.

More preferably the shaft is less than 21 cm with a graduated diameter from proximal to distal ends as shown in FIG. 6.

The shaft for use in adults is preferably approximately between 3 and 5 cm in diameter at its widest proximal end and between 1 and 3 cm at its narrowest distal end.

Other shaft lengths and widths are envisaged for use in smaller or larger patients or for use in paediatrics.

Optionally the exterior of the shaft may have number markings or a graticule to act as a guide and assist the user when inserting and positioning the shaft in the desired location.

Achieving control of instruments during procedures is critical for safe execution as shown in FIG. 1 the shaft 1 includes an internal biopsy channel 4 which provides a controlled passage for surgical instruments such as biopsy forceps or the like.

The biopsy channel 4 is provided inside the shaft 1 and extends from the proximal end of the shaft approximately two thirds of the full length of the shaft. The biopsy channel 4 as may be sized and shaped to receive and guide a variety of different surgical instruments. Surgical instruments are introduced into the biopsy channel 4 and exit the shaft through an opening at the distal end.

Sheathed within the shaft is an inner obturator 3. The obturator helps guide the sigmoidoscope shaft into position and reduce the discomfort of insertion.

The obturator comprises a curved elongate U shaped channel, and a solid tip portion of 0.5 to 5 cm in length. The U shaped channel is sized and shaped to accommodate the biopsy channel 4 within the shaft and to enable the obturator to be withdrawn without: being impeded by; or causing damage to the biopsy channel.

The solid tip protrudes from the distal end of the shaft as shown in FIG. 1 this makes insertion of the shaft into the anus more comfortable. Preferably the solid tip extends between approximately 1-5 cm from the shaft. More preferably the solid tip extends between approximately 2-3 cm from the shaft.

The obturator is sized and shaped to permit it to be easily withdrawn from the shaft after the sigmoidoscope has been inserted into a patient, leaving the shaft in place inside the patient.

The obturator is sized and shaped so that is can be easily withdrawn from the shaft without altering the position of the shaft.

The obturator is formed of a material which has sufficient flexibility to permit it to be easily withdrawn from the shaft without altering the position of the shaft.

In use the rigid disposable shaft 1 of the sigmoidoscope is inserted into the patient's rectum the obturator is withdrawn and discarded and the reusable handle 100 is releasably attached to the shaft 1.

More preferably the tip is hinged or otherwise deformable to allow the obturator to be easily withdrawn from the shaft after the sigmoidoscope has been inserted into a patient.

In an especially preferred embodiment a hinged closure 2 is provided on the tip of the obturator to close the end of the shaft and prevent the shaft becoming blocked with faeces during insertion. After insertion is complete the hinged closure flexes as the obturator is withdrawn from the shaft to allow the obturator to be retracted without damaging or being impeded by the biopsy channel.

Referring to FIGS. 1, 2 4 and 5.

Figure 4:
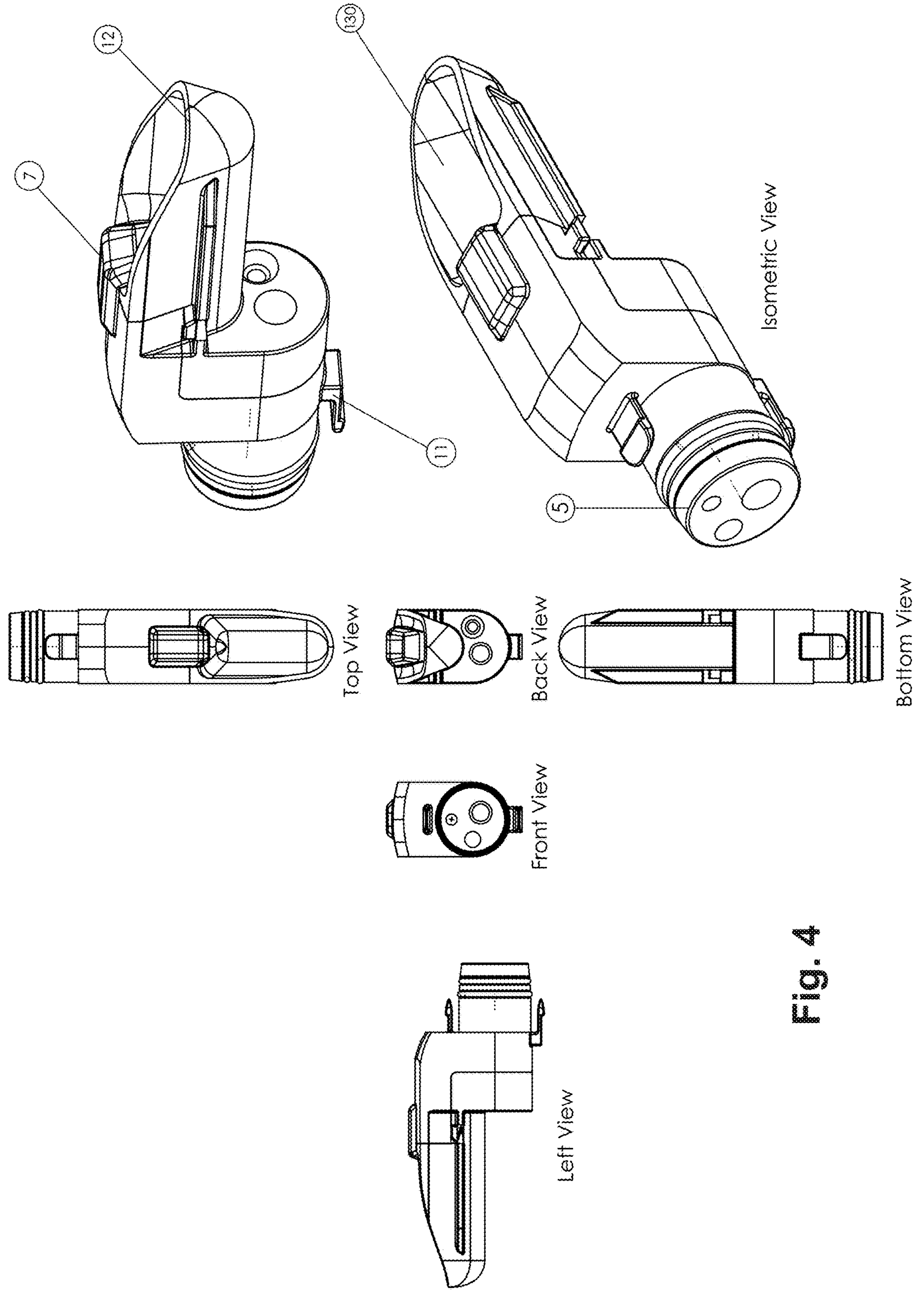
FIGS. 4 and 5 is an exploded view of the manifold assembly from a variety of different angles.
Figure 5:
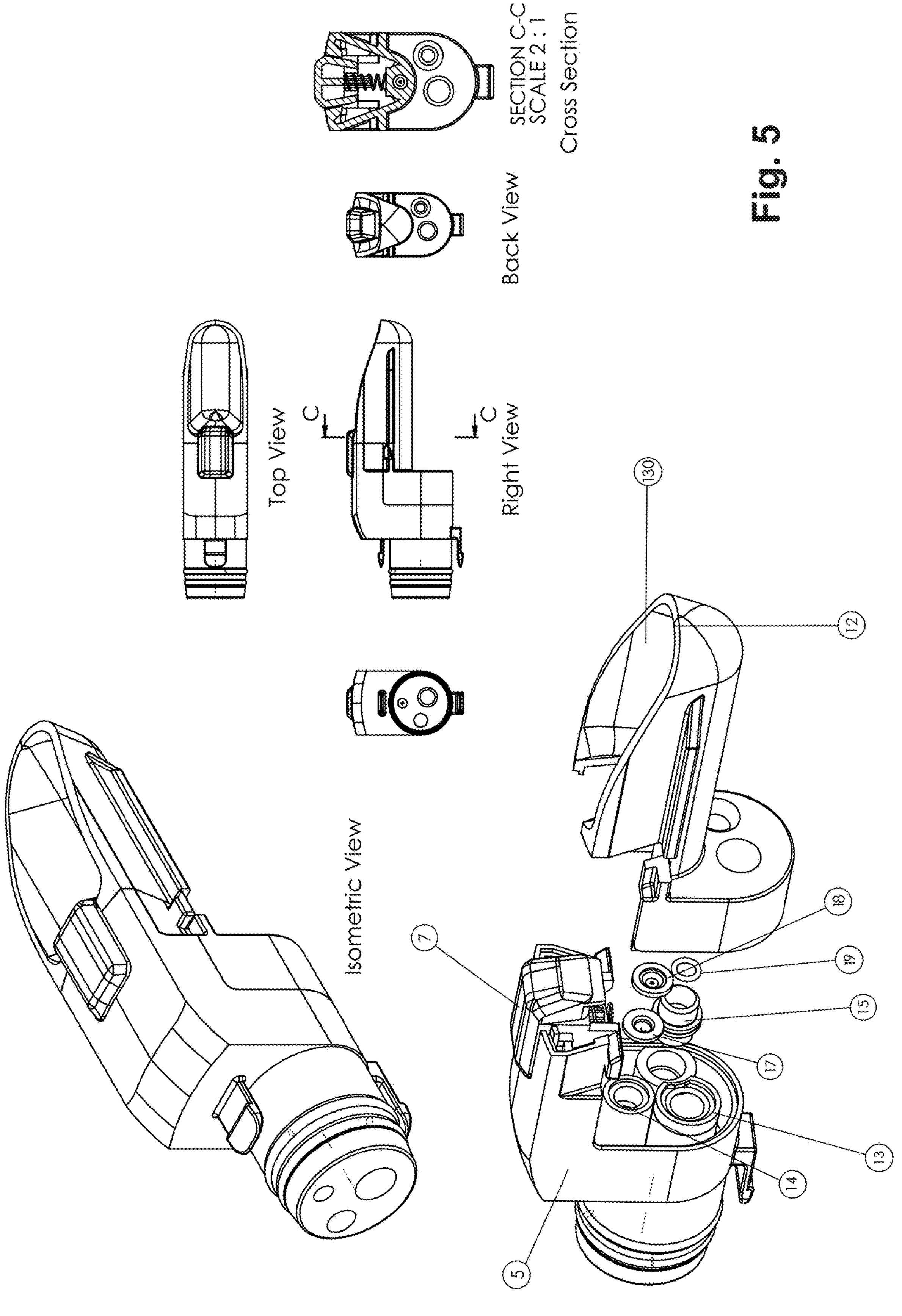

The reusable handle 100 comprises a disposable lumened manifold 5 having 3 or more openings to channels 13, 14 and 15 as shown in FIGS. 4 and 5.

Preferably the disposable lumened manifold 5 is attached to a handgrip 8 by a push-fit arrangement, screw fitting, bayonet fitting or like connection or other types of attachment are also envisaged.

Preferably the push-fit arrangement is provided by an air barb suitably fashioned to prevent air leaks during insufflation.

In an especially preferred embodiment the manifold 5 is releasably attached to the handgrip 8 by means of winged projections 11 along the body of the manifold which integrate with the handgrip 8. In an alternative arrangement the reverse configuration is present, with the winged projections are provided on handgrip 8.

Each of the three or more openings in the disposable lumened manifold 5 shown in FIGS. 4 and 5 are sized and shaped for receiving a device selected from: a camera, a biopsy forceps, a light source, a gas supply, a cauterising tool and a flatus tube.

The one or more channels 13,14,15 are accessed via a biopsy port 130 shown in FIGS. 1 and 5.

Preferably adjacent the biopsy port 130 is a recess formed by a curved wall or lip 12 which improves the control and reduces excessive flapping of the end of the biopsy forceps or other instruments as they are withdrawn from the biopsy channel 4.

This is especially important when retrieving biopsy tissue. As it is difficult to identify the end of the forceps as they are being withdrawn from the biopsy channel and there is a high risk of the end flicking uncontrollably as it is removed leading to the loss of the tissue sample, In a preferred embodiment a dome valve is provided in the manifold 5 to receive biopsy forceps or like surgical instruments. The dome valve forms an air tight seal around the biopsy forceps or like surgical instrument as it is inserted into one or the channels 13, 14 or 15 in manifold 5.

The biopsy forceps are introduced into the manifold through the biopsy port 130. The biopsy forceps extend through the manifold 5 and enter the shaft 1. The biopsy forceps are retained by biopsy channel 4 in the shaft which helps guide the forceps along the shaft to the desired sampling location.

After sampling is complete the biopsy forceps are withdrawn and back pressure closes the dome valve to provide an air tight seal as the forceps or like surgical instrument are removed to prevent contamination on the reusable elements of the sigmoidoscope.

Preferably three channels 13, 14 and 15 are provided in the manifold 5 and are positioned as shown in FIG. 5 at an approximately 120° angle to one another.

The channels may be the same or different sizes. Any suitable arrangement of one or more channel is envisaged. The channels may be equally or unequally spaced.

Each channel may be dedicated to receive a specific single type of device, alternatively a single channel may be sized to receive any one of a number of different devices.

Alternatively, a single channel may receive two or more devices.

Preferably a single channel is shaped and sized to receive a pressurised gas supply and a second device selected from a camera housing, a biopsy forceps, a light source, a flatus tube, and a cauterising/snare coil.

In a preferred embodiment the manifold is provided with a fourth or more additional channels.

Preferably each channel is provided with one or more valve to prevent dirty air and liquid expelled from the colon being introduced into the reusable handle 100

Gas is pumped into the colon to aid viewing. Preferably the gas is air.

Preferably a bellows 6 is provided in the handgrip 8 as shown in FIGS. 1 and 2 for insufflating air into the bowel in a one handed operation.

The air travels to the colon via one or more of the channels.

One or more micro filter is provided in the manifold 5 to prevent dirty air and liquid expelled from the colon being introduced into the reusable handle 100.

Alternatively, one or more micro filter is located in the reusable handle 100 where it can be changed periodically between sessions.

The disposable rigid shaft 1 releasably engages with the reusable handle via the disposable manifold 5.

The disposable manifold 5 releasably engages with the reusable handle 100.

Preferably the reusable handle 100 further comprises a fixed fully encased camera housing channel 24 for receiving a camera lens. The camera channel is introduced into manifold 5 through one of openings 13, 14 and 15 and extends along shaft 1.

Preferably a light source is associated with the camera and moves in concert with camera.

Preferably the light source is an LED light source

Preferably the camera and/or light source are powered by one or more battery (not shown) which is located internal or external to the device so that the device can be used anywhere.

Optionally the one or more lumens is sealed at its distal end to retain the camera or other device within the lumen. Preferably the one or more lumens is sealed with a lens.

In a preferred embodiment two channels 13,14,15 each suited for receiving a camera are provided. The two channels are positioned at an approximately 180° angle to one another.

The first channel being in the 12 O'clock position and the second being in the 6 O'clock position to ensure that a complete 360° view of the lower colon is possible.

Alternatively, in use the sigmoidoscope is rotated to obtain a complete 360° view using a single camera channel. Alternatively, in use the manifold 5 is rotated to obtain a complete 360° view using a single camera channel.

The handgrip 8 is sized and shaped to sit comfortably in the palm of the user.

The sigmoidoscope provides a closed system for insufflating air into a patient. There is no need for an external air supply. The handgrip comprises a self-contained means for supplying air to the shaft 1. Pressurised air is generated by a bellows 6, electric pump, pressurised air cartridge, canister or the like.

Preferably the means for supplying air is partially or fully enclosed within the handgrip. More preferably the means for supplying air is actuated by actuating means located on the handle.

In a preferred embodiment a button not shown in or on the handle may be used to actuate an electric pump or release an air cartridge.

In an especially preferred embodiment pressurised air is provided by a bellows 6 located in a rigid handgrip 8. Preferably the bellows are located fully or partially within the rigid handgrip. In use the bellows are compressed against the handgrip to insufflate air into the patient in a one-handed procedure.

The size of the bellows is chosen to optimise the number of compressions required to insufflate the site to be viewed. The larger the bellows the fewer the compressions required to insufflate. In certain conditions, smaller patients or paediatrics smaller bellows may be preferred to provide greater control of the insufflation.

Preferably a portion of the bellows protrudes from the rigid handgrip 8 and a larger portion of the bellows is contained within a recess in the rigid handgrip. This arrangement enables the bellows to be compressed against a larger surface area of the handgrip during each compression and reduces the number of compressions needed to fully insufflate the patient.

Preferably the bellows are shaped and sized such that when they are urged against the rigid handgrip fewer than 10, more preferably fewer than 5, and more preferably between 1 and 3 compressions are required to fully insufflate the patient.

In a preferred embodiment the bellows have a recess 105 for receiving the index finger of the user to improve grip and therefore safety.

Optionally the handgrip is shaped to include a bump opposite the protruding portion of the bellows for receiving the palm of the user to further improve grip.

A button 7 is provided on the handle for releasing air from the patient at the end of the procedure. Preferably the button 7 is located to enable it to be easily accessible to the users thumb or fore finger.

In use air is pumped into the patient from the sigmoidoscope in a single handed procedure. After the examination and any treatment has been completed the button 7 is released in a single handed procedure and the air is expelled from the patient.

In a first embodiment the handle 100 and the camera housing channel 24 are rigidly connected in a broadly linear arrangement. To enhance user comfort the handgrip 8 is rigidly fixed at a slight angle relative to the camera housing channel 24 and thus in use to the shaft 1 of the sigmoidoscope. Preferably the angle between the handgrip 8 and the camera housing channel 24 is between approximately: 10° and 30° more preferably 15° and 25° more preferably 18° and 23°. More preferably the angle between the handgrip 8 and the camera housing channel 24 is approximately 20°.

In another embodiment an articulating handle portion (not shown) is connected to the fixed camera housing channel 24. Articulation between the handgrip 8 and the camera housing channel 24 may be achieved using deformable, flexible or plastic materials. Alternatively, articulation between the handgrip and the camera housing channel may be achieved by any movable joint. More preferably the joint should be moveable in 3 planes. More preferably the joint is rotatable such as a ball and socket joint, a swivel joint or the like.

Preferably the joint is a ball and socket joint.

In a preferred embodiment the handle portion articulates about a ball and socket joint to aid insertion into the rectum and manipulation thereafter. More preferably the ball and socket joint has a rotation of 20°-25°, 25°-30°, 30°-35°, 35°-40°, 40°-45°, 45°-50°, 50°-55°, 55°-60°, 60°-65°.

More preferably the ball and socket joint has a rotation of approximately 45° to prevent twisting of the handle relative to the shaft.

Preferably the joint has a locking means which can be applied before during or after insertion of the sigmoidoscope. Applying the locking means to restrict the movement of the handle may assist with attachment or removal of the component parts.

More preferably the locking means is located on the handle 100 to enable one handed operation of the sigmoidoscope.

Applying the locking means to restrict the movement of the handle may assist with insertion of the sigmoidoscope into the rectum.

Applying the locking means to restrict the movement of the handle portion may assist with removal of the sigmoidoscope from the rectum.

Applying the locking means to restrict the movement of the handle portion may assist with manipulating, positioning or repositioning the sigmoidoscope to obtain a better, complete or different view of the lower colon.

Applying the locking means to restrict the movement of the handle portion may assist with manipulating, positioning or repositioning the sigmoidoscope when sampling different sites within the lower colon either by taking one or more biopsy or otherwise.

Applying the locking means to restrict the movement of the handle portion may assist with manipulating, positioning or repositioning the sigmoidoscope when treating the patient.

A patient is positioned on an examination couch, preferably in the left lateral position with their knees drawn up and tucked into their chest.

Optionally the device may be inserted with the patient unconscious in a supine or prone position and the user standing by their side.

Suitable lubrication is applied to the anus.

A finger rectal examination is performed to rule out very distal lesions.

A single-use disposable lumened manifold 5 is connected to the reusable handle 100.

A rigid disposable shaft is inserted into the patient's rectum with the tip pointing towards the umbilicus.

The obturator 3 is withdrawn and discarded as clinical waste the camera housing channel 24 is introduced into the shaft and the reusable handle 100 is attached to the shaft via the disposable manifold 5.

Air is insufflated to distend the rectum sufficiently to permit a 360° examination of the bowel but not to cause discomfort to the patient. Using a screen (not shown) as a guide, the scope is manoeuvred to approximately 25 cm from the anal verge. Additional air can be insufflated to aid the view at this depth.

The scope is withdrawn preferably at a rate of 0.5 cm per second and a 4-quadrant examination of the bowel is performed every 3 cm by rotating the handle circumferentially.

Insertion, insufflation, withdrawal, rotation and release of the air are all performed in a one handed operation.

If a lesion or abnormal cells are identified, a conventional flexible pre-existing biopsy forceps may be inserted into manifold 5 through biopsy port 130. Tissue is sampled or removed in its entirety and retrieved through the biopsy port 130.

If a lesion or abnormal cells are identified, a range of different conventional surgical instruments such as by way of example only snare forceps, catheter, Raphaelo radio frequency ablation probe etc may be introduced into manifold 5 via one of channels 13, 14 or 14. The instrument is guided along the shaft 1 by biopsy channel 4 to the desired site and the tissue ablated or otherwise treated.

After the examination and any treatment has been completed button 7 is released in a single-handed procedure and the air is expelled from the patient through one of the channels 13,14,15.

The camera housing channel 24 camera, and handgrip are released from the shaft and withdrawn from the patient either as a single unit or separately.

The disposable manifold 8 and shaft 1 are withdrawn from the patient's anus as a single unit and discarded as clinical waste.

The procedure is easy and comfortable for both the patient and the clinician or user.

The camera and handgrip are minimally cleaned preferably with Tristel™ trio anti-sporicidal wipes or the like.

The present invention provides a digital device which can be used to examine, the anus rectum and lower colon and permit abnormal tissue to be sampled or treated in a cost-efficient, rapid, safe, and convenient manner by trained clinicians of either low skill or high skill, in general practice, community or hospital settings.

The device is safe and comfortable to use for both the patient and the user it provides excellent visualisation of the lower colon in a primary healthcare setting and thus has the potential to reduce colonoscopy referrals.

High quality digital images captured using the invention can be shared or stored on any USB enabled device.

The digital images captured using the invention can be used by clinicians to survey, monitor and make new diagnoses.

Sharing the digital images enables diagnosis and/or training to be provided remotely.

The digital images obtained using the invention can be used train individuals or machines in how to recognise one or more disease of the lower colon.

The invention is portable, easy to train and permits immediate examination which improves patient experience and compliance.

The invention is portable, easy to train and permits immediate examination which improves patient experience and compliance.

The following is a non-exhaustive list of embodiments:

1. A reusable rigid scope comprising:
   - a head portion for releasable attachment to: a conventional single use rigid sigmoidoscope;
   - a single use lumened manifold; and
   - an articulated handle.
2. A scope as claimed in claim 1 wherein the articulated handle is lockable.
3. A scope as claimed in claim 1 or claim 2 wherein the articulated handle comprises a ball and socket joint.
4. A scope as claimed in any preceding claim further comprising bellows.
5. A scope as claimed in any preceding claim wherein the lumened manifold comprises one or more channel for receiving one more of: a camera; a biopsy forceps, a source of pressurised gas a flatus tube, a cauterising coil and a light source.
6. A scope as claimed in claim 5 wherein the pressurised gas is air.
7. A scope as claimed in any preceding claim further comprising one or more of: a lens; a light source; a one way valve; a port for accessing the one or more channel of the lumened manifold; and an air filter.
8. A single use lumened manifold for use with a reusable rigid scope as claimed in any preceding claim.
9. A scope as claimed in any preceding claim for use in a one-handed method of internal examination of the lower colon.
10. A scope as claimed in any one of claims 1 to 8 for use in the sampling of the rectum and sigmoid colon.
11. A method of treatment comprising inserting a scope as claimed in any one of claims 1 to 8 into the lower colon and sampling, biopsying, removing, cauterizing or otherwise treating the lower colon.
12. A method of diagnosis comprising inserting a scope as claimed in any one of claims 1 to 8 into the lower colon, viewing, biopsying or otherwise examining the lower colon, comparing the results with images or biopsies of known normal lower colon to diagnose disease.

The invention claimed is:

1. A rigid scope comprising:

a rigid shaft; and a handle for releasable attachment to the rigid shaft, the handle comprising:

a detachable lumened manifold configured to couple to the rigid shaft at a distal end, the detachable lumened manifold comprising a plurality of channels, each of the plurality of channels being fluidically isolated from one another;

a straight distal portion configured to detachably couple the handle with a proximal end of the detachable lumened manifold, the straight distal portion being aligned with a longitudinal axis of the rigid shaft;

an angled proximal portion configured to extend at an angle relative to the straight distal portion; and a bellows configured to be compressible to insufflate air through at least one of the plurality of channels in the detachable lumened manifold into a rectum of a patient, wherein each of the plurality of channels is configured to form a unidirectional sealed barrier that prevents air or fluid contamination from reaching the straight distal portion.

2. The rigid scope of claim 1, wherein the plurality of channels are configured to receive one or more of a camera, a surgical instrument, a biopsy forceps, air from the bellows, a cauterizing coil and a light source.

3. The rigid scope of claim 2, wherein at least one of the plurality of channels further comprises a one-way valve.

4. The rigid scope of claim 3, wherein the one-way valve is a dome valve.

5. The rigid scope of claim 2, wherein the plurality of channels comprises one or more microfilters.

6. The rigid scope of claim 2, further comprising one or more of a lens and a port for accessing the plurality of channels.

7. The rigid scope of claim 1, further comprising a gas releaser for use in releasing gas from a patient.

8. The rigid scope of claim 1, wherein one or both of the rigid shaft and the detachable lumened manifold are single use.

9. The rigid scope of claim 1, wherein the rigid shaft is tapered such that a proximal end of the rigid shaft has a diameter which exceeds the diameter of a distal end of the rigid shaft.

10. The rigid scope of claim 1, wherein the rigid shaft and the handle are arranged at an approximately 20° angle to one another.

11. The rigid scope of claim 1, wherein the rigid shaft further comprises a biopsy channel.

12. The rigid scope of claim 1, wherein the rigid shaft further comprises a graticule.

13. The rigid scope of claim 1, wherein the bellows includes a recess configured to receive a finger of a user for improved grip of the handle.

14. The rigid scope of claim 1, wherein the detachable lumened manifold includes a button thereon for releasing air from the patient.

15. The rigid scope of claim 1, wherein the plurality of channels comprises a first channel, a second channel, and a third channel, and the first channel, second channel, and third channel are positioned at an approximately 120° angle to one another.

16. The rigid scope of claim 1, wherein each of the plurality of channels comprises a one-way valve covering a cross-section of each of the plurality of channels, the one-way valve being configured to provide a unidirectional seal that prevents backward flow of air or fluid toward the bellows.

17. A method of treatment comprising:

inserting into a lower colon a rigid scope comprising a rigid shaft, a handle for releasable attachment to the rigid shaft, the handle comprising a detachable lumened manifold configured to couple to the rigid shaft at a distal end, the detachable lumened manifold comprising a plurality of channels, each of the plurality of channels being fluidically isolated from one another, a straight distal portion configured to detachably couple the handle with a proximal end of the detachable lumened manifold, the straight distal portion being aligned with a longitudinal axis of the rigid shaft, an angled proximal portion configured to extend at an angle relative to the straight distal portion; and a bellows being compressible to insufflate air through at least one of the plurality of channels in the detachable lumened manifold into a rectum of a patient, wherein each of the plurality of channels is configured to form a unidirectional sealed barrier that prevents air or fluid contamination from reaching the straight distal portion; and sampling, performing biopsy, removing, cauterizing or otherwise treating the lower colon.

18. A method of anorectal diagnosis comprising:

inserting a rigid scope into an anus, rectum or lower colon of a patient, wherein the rigid scope comprising a rigid shaft, a handle for releasable attachment to the rigid shaft, the handle comprising a detachable lumened manifold, the detachable lumened manifold detachably coupled to the rigid shaft at a distal end of the detachable lumened manifold, the detachable lumened manifold comprising a plurality of channels, each of the plurality of channels being fluidically isolated from one another, a reusable handgrip comprising a straight distal portion having a first recess configured to detachably couple the handgrip with a proximal end of the detachable lumened manifold and an angled proximal portion, wherein the angled proximal portion extends at an angle relative to the straight distal portion of the handgrip, and the straight distal portion is aligned with a longitudinal axis of the rigid shaft, and a bellows being compressible to insufflate air through at least one of the plurality of channels in the detachable lumened manifold into a rectum of a patient, wherein each of the plurality of channels configured to form a unidirectional sealed barrier that prevents air or fluid contamination from reaching the reusable handgrip, and wherein the handle includes a first side and an opposed second side with the first side having a second recess configured to couple the handgrip with the bellows and the opposed second side having a recessed port for introduction of a surgical instrument into the rigid shaft;

viewing, performing biopsy or otherwise examining the anus, rectum or lower colon and generating test results for the anus, rectum or lower colon, and comparing the test results with images or biopsies of known normal anus, rectum or lower colon to form a disease diagnosis.

19. The method of claim 18, further comprising treating the anus, rectum or lower colon according to the disease diagnosis.

20. The method of claim 18, wherein the plurality of channels are configured to receive one or more of a camera, a surgical instrument, a biopsy forceps, air from the bellows, a cauterizing coil and a light source.

21. The method of claim 18, further comprising a gas releaser for use in releasing gas from a patient.

22. The method of claim 18, wherein the rigid shaft is tapered such that a proximal end of the rigid shaft has a diameter which exceeds the diameter of a distal end of the rigid shaft.

23. A rigid scope comprising:

a rigid shaft; and a handle for releasable attachment to the rigid shaft, the handle comprising:

a detachable lumened manifold detachably coupled to the rigid shaft at a distal end of the detachable lumened manifold, the detachable lumened manifold comprising a plurality of channels, each of the plurality of channels being fluidically isolated from one another;

a reusable handgrip comprising a straight distal portion having a first recess configured to detachably couple the handgrip with a proximal end of the detachable lumened manifold and an angled proximal portion, wherein the angled proximal portion extends at an angle relative to the straight distal portion of the handgrip, and the straight distal portion is aligned with a longitudinal axis of the rigid shaft; and a bellows configured to be compressed to insufflate air through at least one of the plurality of channels in the detachable lumened manifold into a rectum of a patient, wherein each of the plurality of channels is configured to form a unidirectional sealed barrier that prevents air or fluid contamination from reaching the reusable handgrip, and wherein the handle includes a first side and an opposed second side with the first side having a second recess configured to couple the handgrip with the bellows and the opposed second side having a recessed port for introduction of a surgical instrument into the rigid shaft.

24. The rigid scope of claim 23, wherein the bellows includes a recess configured to receive a finger of a user for improved grip of the handle.

25. The rigid scope of claim 23, wherein the detachable lumened manifold includes a button thereon for releasing air from the patient.

26. The rigid scope of claim 23, wherein the handgrip extends at an angle relative to the detachable lumened manifold.

27. The rigid scope of claim 23, wherein each of the plurality of channels comprises a one-way valve covering a cross-section of each of the plurality of channels, the one-way valve being configured to provide a unidirectional seal that prevents backward flow of air or fluid toward the bellows.

* * * * *